United States Patent [19]

Dogliotti

[11] 4,105,801

[45] Aug. 8, 1978

[54] COATED EDIBLE PRODUCT AND PROCESS FOR MAKING SAME

[75] Inventor: Amilcare Dogliotti, Neive (Cuneo), Italy

[73] Assignee: P. Ferrero & C. S.p.A., Alba (Cuneo), Italy

[21] Appl. No.: 770,146

[22] Filed: Feb. 18, 1977

[30] Foreign Application Priority Data

Mar. 5, 1976 [IT] Italy ............................... 67534 A/76

[51] Int. Cl.² ............................................. A23G 3/00
[52] U.S. Cl. ..................................... 426/99; 426/103; 426/548; 426/613; 426/660; 426/804
[58] Field of Search ................. 426/99, 103, 548, 613, 426/660, 804

[56] References Cited

U.S. PATENT DOCUMENTS

| | | | |
|---|---|---|---|
| 2,461,399 | 2/1949 | Strausser | 426/103 |
| 2,682,471 | 6/1954 | Alther | 426/103 |
| 3,769,039 | 10/1973 | Kleinert | 426/660 |
| 3,914,434 | 10/1975 | Bohni | 426/548 |
| 3,958,024 | 5/1976 | Fissolo | 426/660 |

FOREIGN PATENT DOCUMENTS 582,566  9/1959  Canada ..................................... 426/660

Primary Examiner—Jeanette M. Hunter
Attorney, Agent, or Firm—Sughrue, Rothwell, Mion, Zinn and Macpeak

[57] ABSTRACT

In a dragée comprising a core portion and a shell adheringly enveloping the core portion, the shell is formed by an intimate mixture of microcrystals of xylitol with a normally solid fatty substance in a proportion of 0.5 to 15 parts by weight of fatty substance to each 100 parts by weight xylitol. The fatty substance preferably consists of cocoa butter.

24 Claims, No Drawings

COATED EDIBLE PRODUCT AND PROCESS FOR MAKING SAME

The present invention concerns coated edible products hereinafter briefly called "dragées." The invention is of particular interest to the confectionery field but is equally applicable to other fields, in particular to coated pharmaceutical pills.

The coating process for obtaining dragées consists basically of introducing into a rotary basin or bowl a batch of preformed bodies, called "cores," and forming upon each of said cores an adherent shell of solid material, which latter is supplied to the bowl in the form of a fine spray while the bowl is maintained in slow rotation. Suitable coating apparatus, which are also suitable for the purposes of this invention, are disclosed by British patent specification Nos. 922,495 and 1,047,349, for example.

The purpose of the shell can be that of preserving the core from physico-chemical agents (for example atmospheric air, humidity) and mechanical agents (shocks, abrasions), or also that of imparting to the product a particular taste or nutritional value. The most typical shells, at least in the confectionary sector, consist of sugar (saccharose) with eventual addition of flavorings. A sugar shell is compact, smooth, abrasion- and shock resistant, adherent well to the core, and sweetens the product. Among the most typical products coated with a sugar shell, almond candies and chewing gum can be mentioned. Several pharmaceutical products also, in the form of tablettes or pills, present a sugar shell.

However, in many instances, sugar is undesirable (for example for medical-dietetical reasons). Besides, the sweet taste of sugar is not agreeable to many consumers in the hot season; a sweet but refreshing taste, not attainable with saccharose, would be very desirable.

It is known that, in the alimentary field in general and in particular in the confectionery field, saccharose is often replaced by polyalcohols, especially by sorbitol. However, as regards dragées, sorbitol can be successfully used only as an ingredient for the core and not for the shell, because of its hygroscopicity. While studying the problem, the applicant has taken into consideration another polyalcohol and precisely the xylitol

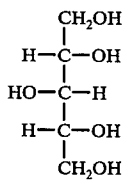

commercially available both in solid form and in the form of aqueous concentrated solutions. However, contrary to the saccharose shell, that of xylitol deteriorates rapidly with time. In particular, already after a few hours a xylitol shell cracks and its outer surface initially smooth becomes wrinkled; at the same time even the intimate constitution of the shell, initially sufficiently microcrystalline, changes into a course, rough structure fastidious to the palate and in chewing. A xylitol shell offers the peculiar advantage of being refreshing to the mouth (owing to an appreciable negative heat of solution); however this advantage does not compensate the aforesaid drawbacks.

The present invention is based on the discovery that it is possible to obtain a xylitol shell of extremely microcrystalline structure and "to stabilize" such a shell in a surprisingly efficacious way, thereby maintaining in practice indefinitely the microcrystalline structure, compactness and smooth aspect of the outer surface thereof.

Therefore, an object of this invention consists of a dragée, especially (but not exclusively) of a confectionery dragée, characterized in that the shell enveloping the core consists of an intimate mixture of microcrystals of xylitol with a normally solid fatty substance in a proportion of 0.5 to 15 parts by weight of the fatty substance per 100 parts by weight of xylitol (computed as anhydrous).

There is reason to think that the fatty substance isolates each microcrystal and thusly prevents all the alterations which, instead, unavoidably occur when the microcrystals are in reciprocal contact. Optimum results are attained with 1–2 parts by weight of the fatty substance to 100 parts by weight of xylitol. However, since xylitol is a relatively expensive product, it may be economically convenient to increase the amount of the fatty substance, up to a maximum limit of 15 parts by weight as hereinbefore indicated, without prejudice to the shell.

Xylitol, which is a polyalcohol, must not necessarily be chemically pure. It may eventually contain other polyalcohols, in particular sorbitol and/or mannitol, provided that their total content does not exceed 5% by weight.

Preferably the fatty substance is selected among the mono-, di- and triglycerides of the fatty acids, in particular palmitic-, stearic- and oleic acids.

Fatty substances which melt between 20° and 60° C are suitable, but those which melt between about 35° and about 42° C are preferred, that is those which are solid at environmental temperatures as high as about 30° C but which melt in the consumer's mouth. The fatty substances, normally solid, for alimentary use, do not usually present a sharp melting point because they are not chemically homogeneous; for the purposes of the present invention it is advisable to give the preference to those fatty substances (mixtures of mono-, di- and/or triglycerides), which have a narrow melting range, advantageously not exceeding about 7° C, as opposed to those wherein the effective melting point is preceded by a long softening interval (pasty and semiliquid state).

Therefore those mixtures of glycerides are preferred which exhibit a strong prevalence of a determined glyceride. Mono- and diglycerides suitable for the purposes of this invention may present a melting point ranging from about 40° to about 70° C, keeping in mind that the melting point can be lowered (owing to formation of eutectics) by addition of a triglyceride having a convenient melting point. The preferred fatty substance is cocoa butter which, as is known, melts around 35° C.

The shell thickness may obviously be selected at will. In the case of products in the form of tablettes or pills of a diameter ranging from about 5 mm to about 10 mm the typical thickness values are of the order of 0.3–0.8 mm. If the core is relatively soft and/or the dimensions are larger, the thickness value is selected conveniently greater.

The cores can be selected among a great variety of edible materials, as in the case of dragées having a saccarose shell. Thus one can use almonds, chunks of licorice, candies of various kinds, gums, jellies, bonbons cast in starch moulds, pop-corn (preferably that obtained from corn dough because of a more regular form), tablettes obtained by compression of various baked or agglomerated masses, etc. The core may contain, as a sweetener, saccharose, sorbitol, mannitol and/or xylitol. In the case of pharmaceutical products the core will be (in the typical cases) prevalently constituted by the excipient, which may be solid or gummy, without any prejudice. In certain cases, for example when the core contains hygroscopic substances (as for example, sorbitol) it is advisable to coat it previously with a thin anchoring layer for the shell; as an anchoring material, gum arabic and tragacanth gum are particularly indicated.

An object of the present invention resides also in a process for manufacturing a dragée hereinbefore described, mainly characterized in that a batch of the cores for the dragées is submitted to coating with the use of an acqueous concentrated xylitol solution having dispersed therein the fatty substance, said solution (called afterwards "syrup") being sprayed over the batch at a temperature at which said fatty substance is in its molten or superfused state while the batch is tumbled and maintained at a temperature lower than, or at the utmost equal to, the melting point of the fatty substance.

In practice, any coating machine having a rotary bowl or cylinder in which the cores are tumbled, as used hitherto for coating with saccharose, can be used in the process according to the present invention. The basic difference lies in the composition of the syrup and in the operating conditions of the coating machine.

In order to prepare the syrup, 100 parts by weight of anhydrous xylitol may be dissolved in 20, up to 60, parts by weight of water. If commercial concentrated liquid xylitol is used the water proportion should be adjusted according to the hereinbefore indicated ratio. The fatty substance is emulsified in the solution by maintaining the temperature of the latter above the melting point of the fatty substance and adding the substance preferably already in the molten state. The amount is that defined hereinbefore, that is 0.15-15 parts by weight of fatty substance to 100 parts by weight of xylitol. It is to be noted that triglycerides are hydrorepellent and thus a purposedly added emulsifier is necessary, while mono- and diglycerides of alimentary fatty acids $C_{14}$-$C_{18}$ contain —OH groups and act themselves as emulsifiers. For example, "Emulsifier No. 350" contemplated by the existing food regulations is a mixture of monoglycerides of alimentary fatty acids $C_{14}$-$C_{18}$ (exclusive of lauric acid). The amount of emulsifier added may vary, thus, from zero, when the fatty substance contains sufficient proportions of mono- and/or diglycerides, up to a maximum value which is about 1 part by weight per 100 parts of xylitol when 15 parts by weight of a triglycerid have to be emulsified. For example, for 1 part by weight of cocoa butter, usually 0.1 part by weight of "Emulsifier No. 350" are suitable. Should the syrup thus obtained be excessively fluid for actual use, a thickening agent may be added in a proportion of 3-20 parts by weight to each 100 parts xylitol. The preferred thickening agents are those capable of promoting the adhesion of the particles forming the shell, that is the compactness of the shell. The preferred thickening agents are, thus, animal gelatines, vegetable gums, gelatinized or chemically converted starches and also natural starches. An excellent thickener is gum arabic, generally in the amount of 4-5 parts by weight per each 100 parts by weight xylitol.

The operating process comprises a determined number of substantially identical "cycles" which follow one another while the bowl of the coating machine is rotating. Each cycle comprises a first stage, wherein a certain amount of syrup, which can vary from 0.2 kg to about 1 kg per 100 kg of cores charged into the bowl, is sprayed over the charge. The duration of the first stage is of, at least, 5 seconds and may even amount to 30 seconds, typically to 15-20 seconds. In this way, also taking into account the rotational speed of the bowl, the syrup is substantially distributed uniformly over the entire batch of cores forming on each of the latter a skin having a somewhat "rough" aspect. In the subsequent stage, called a smoothing stage, the bowl continues to revolve for 30-150 seconds, whereby the skin on the cores bocomes smoother. In the subsequent stage, which may last from 1 to 10 minutes (generally 2-3 minutes) air, heated at 25°-50° C, typically at 30°-35° C, is blown into the bowl, whereby the skin on the cores is dried. About 10 cbm/min of air to 100 kg of loaded cores are suggested as a suitable flow rate. Finally a slowing down or calming stage of 30-60 seconds follows, in the course of which the air fan is stopped and the atmosphere inside the bowl becomes quiescent. At this point the cycle is repeated. The number of cycles depends on the thickness of the shell to be attained. In general a minimum of 10 cycles is needed but in the case of dragées of a large diameter and thick shells even 500 cycles may be necessary. In any event, at the end of the process the coated product is discharged from the bowl ready for packing.

EXAMPLE 30 kg of lenticular shaped cores, having a diameter ranging from 4.7 to 5 mm are charged into a bowl of a coating machine having a diameter of 70 cm and rotating on an inclined axis.

The syrup is prepared from 100 parts of anhydrous xylitol, 35 part water, 1 part cocoa butter, 0.1 parts Emulsifier No. 350 and 4 parts gum arabic as a thickener. The parts are by weight. The temperature of the syrup fed to the spray nozzles of the coating machine is 55° C. The bowl revolves at 28 r.p.m. In the first spraying stage 0.1 kg of syrup are sprayed in 5 seconds. The smoothing stage lasts 30 seconds. Air, heated at 30° C is fed for 1 minute during the drying stage. After a calming stage of 1 minute the cycle is repeated from the beginning and so on for a total of 7 hours, care being taken to progressively increase the amount of syrup in the spraying stages up to a final value of 0.7 kg and to progressively extend the spraying stages to 20 seconds, the smoothing stages to 110 seconds and the drying stage to 3 minutes. During all cycles the temperature of the batch in the bowl is below 30° C. At the end the dragées unloaded from the bowl present a diameter of 5.5-5.7 mm and as a result are coated with a compact, adherent shell of an extremely homogeneous microcrystalline xylitol. Except for the water which has been removed by evaporation during the process, the shell composition corresponds to that of the syrup. The shell surface is smooth and presents a silky brilliance. After 2 months stockage of the product the shell was absolutely unchanged and no sticking or agglomeration of the dragées occurred.

I claim:

1. A dragée comprising a core and shell of edible material enveloping the core and adhering to the latter, wherein the shell is formed by an intimate mixture of microcrystals of xylitol with a normally solid fatty substance selected from the group consisting of mono-, di- and triglycerides of palmitic-, stearic- and oleic acids and cocoa butter, in a proportion of 0.5 to 15 parts by weight of the fatty substance to each 100 parts by weight of xylitol.

2. A dragée according to claim 1, wherein the fatty substance is selected from the group consisting of mono-, di-, and triglycerides of palmitic-, stearic- and oleic acids.

3. A dragée according to claim 1, wherein said fatty substance melts between 20° and 60° C.

4. A dragée according to claim 3, wherein said fatty substance presents a narrow melting range not exceeding 7° C.

5. A dragée according to claim 2 wherein said fatty substance mainly consists of triglycerides having a melting point from 20° to 60° C and in a minor proportion mono- and diglycerides having a melting point from 40° to 70° C.

6. A dragée according to claim 1, wherein said fatty substance is cocoa butter.

7. A dragée according to any of claims 1, wherein the shell contains 1 part by weight of said fatty substance to each 100 parts by weight of xylitol.

8. A dragée according to claim 3, wherein said fatty substance melts between 35° and 42° C.

9. Process for preparing dragées comprising a core and a shell of edible material enveloping the core and adhering to the latter, characterized in that a batch of the cores is submitted to coating with the use of a concentrated aqueous solution of xylitol having dispersed therein a normally solid fatty substance in a proporation of 0.5 to 15 parts by weight of the substance per each 100 parts by weight xylitol, wherein said normally solid fatty substance is selected from the group consisting of mono-, di- and triglycerides of palmitic-, stearic- and oleic acids and cocoa butter, said solution being sprayed over the batch at a temperature at which said fatty substance is in a molten or superfused state, while the batch is tumbled and maintained at a temperature lower than or at most equal to the melting point of the fatty substance.

10. Process according to claim 9, wherein said solution contains an emulsifier for said fatty substance.

11. Process according to claim 10, wherein the emulsifier is contained in an amount up to 1 part by weight to 100 parts xylitol.

12. Process according to claim 9, wherein said solution also contains a thickener.

13. Process according to claim 12, wherein the thickener is contained in an amount of 3-20 parts by weight to 100 parts xylitol.

14. Process according to claim 9, wherein the solution contains 100 parts by weight xylitol (computed on anhydrous basis) per 20-60 parts by weight water.

15. Process as claimed in claim 9, wherein the normally solid fatty substance is selected from the group consisting of mono-, di- and triglycerides of palmitic, stearic and oleic acids.

16. Process as claimed in claim 9, wherein the fatty substance melts in the range of 20° to 60° C.

17. Process as claimed in claim 16, wherein the fatty substance melts in the range of 35° to 42° C.

18. Process as claimed in claim 9, wherein the fatty substance has a narrow melting range not exceeding 7° C.

19. Process as claimed in claim 15, wherein the fatty substance has a major proportion consisting of triglycerides having a melting point from 20° to 60° C, and the remaining minor proportion consisting of mono- and diglycerides having a melting point from 40° to 70° C.

20. Process as claimed in claim 9, wherein the fatty substance is cocoa butter.

21. Process as claimed in claim 9, wherein the solution contains 1 part by weight fatty substance per 100 parts by weight xylitol.

22. Process according to claim 9, wherein said solution consists of 100 parts by weight of xylitol, 35 parts of water, 1 part of cocoa butter, 0.1 part of emulsifier and 4 parts of gum arabic as a thickener.

23. Process according to claim 12, wherein said thickener is selected from the group consisting of animal gelatins, vegetable gums, gelatinized or chemically converted starch and natural starch.

24. Process according to claim 12, wherein said thickener is gum arabic.

* * * * *